United States Patent [19]

Baker

[11] 4,297,587
[45] Oct. 27, 1981

[54] ABSOLUTE DC SYSTEM FOR A LASER INSPECTION SYSTEM

[75] Inventor: Cole H. Baker, Westport, Conn.

[73] Assignee: Intec Corporation, Trumbull, Conn.

[21] Appl. No.: 128,286

[22] Filed: Mar. 7, 1980

[51] Int. Cl.³ .............................................. G01N 21/30
[52] U.S. Cl. .............................. 250/563; 250/214 AG
[58] Field of Search ................. 250/214 AG, 562, 572, 250/563; 356/431, 444

[56] References Cited

U.S. PATENT DOCUMENTS

| | | | |
|---|---|---|---|
| 3,866,054 | 2/1975 | Wolf | 250/562 |
| 3,900,265 | 8/1975 | Merlen et al. | 356/200 |
| 3,958,127 | 5/1976 | Faulhaber et al. | 250/563 |

*Primary Examiner*—David C. Nelms
*Assistant Examiner*—Darwin R. Hostetter
*Attorney, Agent, or Firm*—Parmelee, Johnson, Bollinger & Bramblett

[57] ABSTRACT

A laser inspection system is provided having an absolute closed loop dc system in which the power gain is automatically stabilized. In order to stabilize the power gain of the system and provide a closed loop absolute reference dc level, a sample of the radiation from the laser beam utilized to scan the material being inspected is applied to a photomultiplier tube for generating a reference pedestal signal which is dependent on the intensity of the laser beam and is free of the influence of the characteristics of the material being inspected. The reference pedestal signal is applied to a comparator which develops a control signal which is applied in a single closed feedback loop including in effect, the laser source and the light collection and detection system within the loop. This loop includes the photomultiplier tube and its high voltage power supply to which the control signal is applied for stabilizing the gain of the system. Accordingly, if the sensitivity of the receiver varies, the photomultiplier drifts, drift occurs in the power supply, and/or the laser beam intensity drifts, the feedback loop will detect such changes and compensate for them, to produce an absolute, stable dc system.

7 Claims, 5 Drawing Figures

ABSOLUTE DC SYSTEM FOR A LASER INSPECTION SYSTEM

BACKGROUND OF THE INVENTION

This invention relates to a stabilized absolute direct current laser inspection system, and more particularly to such a system with a single feedback loop which can compensate for changes in the laser light source and the light collection system such that the flaw signals produced by the system are influenced by the product inspected and not the system which is doing the inspecting.

In light inspection systems, radiation, for example, in the form of a laser beam, is scanned successively across the surface of material being examined and the intensity of the beam either reflected, transmitted or scattered from the material is detected by a receiver which includes a photomultiplier tube. The signal generated by the photomultiplier tube is called the product pedestal signal which varies in accordance with the characteristics of the material being examined thereby offering a method of determining whether flaws exist in the material or not by variations in the signal detected. The product pedestal signal also includes a certain dc level which will be present based on the intensity of the laser beam, system sensitivity, etc., regardless of the type of materials being examined or whether flaws exist in the material or not. This signal may be referred to as the background signal or the dc level of the system which in effect does not depend on product changes but rather on inspection system variations. For many applications, a relative change in the signal level is all that is required for determining flaws while in certain types of web products absolute changes are required for the purposes of identifying flaws. In the latter application, the background signal level of the system must be stabilized in order that changes in the product pedestal level will be reflected only by changes in the characteristics of the material being examined.

SUMMARY

Accordingly, it is an object of this invention to provide a new and novel stabilized absolute direct current laser inspection system which is simple in implementation and capable of measuring absolute changes in product characteristics.

Another object of this invention is to provide a new and improved laser scanner flaw detection system in which the signal utilized for stabilization is free of external environmental considerations.

In carrying out this invention in one illustrative embodiment thereof, a laser inspection system is provided having a scanner for scanning a laser beam over a target being inspected which is a moving web of material. A receiver is provided for collecting laser beam radiation emanating from the web and the receiver includes a photomultiplier tube for detecting and generating signals in accordance with the intensity of radiation applied thereto. A sample of the radiation from the laser beam is taken from the scanner and applied directly to the photomultiplier tube for generating a reference pedestal signal which is dependent on the intensity of the laser beam but free of material or product influences. The reference pedestal signal is compared to a reference signal for deriving a control signal which is applied to a closed loop including the power supply for the photomultiplier tube which regulates the power gain of the high voltage power supply to thereby provide a stabilized absolute dc system.

The sample of radiation in one form may be applied to the photomultiplier tube by a light pipe, or in another form by a stabilized sensor which is scanned by the laser beam for converting the light signal of the laser beam into electrical form which is amplified and applied to a temperature compensated light emitting diode which is in communication with the photomultiplier tube.

Advantageously, the positioning of the light pipe or the detector in proximity of the scanner avoids any excess overscan in the system as well as removes the receiving end of the light pipe or the detector from the influences of the external environment.

BRIEF DESCRIPTION OF THE DRAWINGS

The invention, together with further aspects, objects and advantages thereof, will be better understood from the following description taken in connection with the accompanying drawings.

DESCRIPTION OF THE PREFERRED EMBODIMENTS

Figure 1:
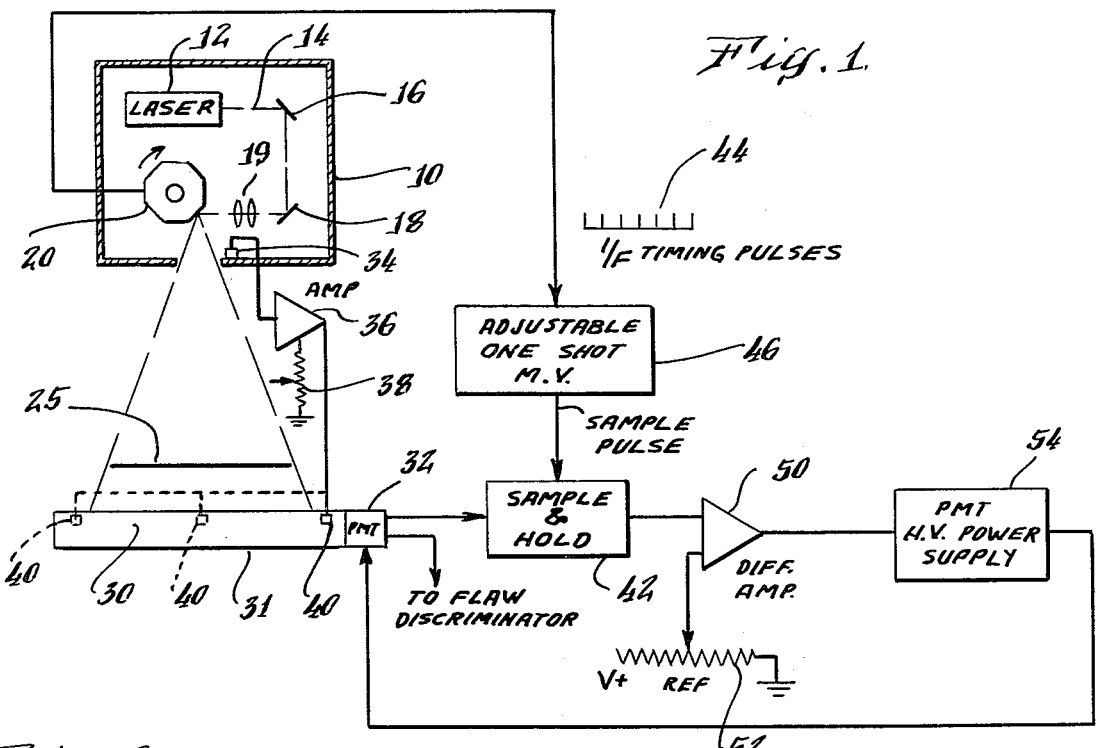
FIG. 1 is a schematic block diagram of the stabilized absolute direct current laser inspection system embodied in the present invention.

In the following description, like elements will bear the same reference numerals. Merely of purposes of illustration a transmissive type system is illustrated in which flaws are detected based on the transmissive properties of the material being examined. However, a reflective type system where the output of the system is proportional to the reflectivity of the spot on which the laser beam is impinging may also be utilized in which case the receiver would be positioned above the target. Whether a transmissive or a reflective or scattering mode is utilized will depend upon the application and the type of material which is being examined.

Referring now to FIG. 1, a scanner referred to generally with the reference character 10 includes a suitable source of radiation, for example, a light beam 14 generated by a laser 12 which is applied after reflection from folded mirrors 16 and 18 and through spot forming optics 19 to a rotary scanner 20. The rotary scanner 20 is a conventional multi-facet mirrored surface polygon which is driven by a motor (not shown) in the direction of the arrow on the drawing. It will be apparent that the laser along with the folded mirrors and the spot forming optics may be positioned external of the scanner 10. It will also be apparent that different types of scanners may be employed, for example oscillating mirrors, rotating prisms, etc. The rotary scanner 20 performs the function of successively scanning the beam 14 across a continuously moving web of material 25 which is moving in a direction orthogonal to the plane of the drawing. The rotary scanner 20 causes the beam 14 to scan across the surface of the material 25 and scanning in the orthogonal direction to create a raster is accomplished automatically by the movement of the web of material 25. Light transmitted through the material 25 is applied to a receiver 30 having a suitable detector therein such as a photomultiplier tube (PMT) 32 which detects the light applied thereto. Although different types of receivers may be utilized, the type illustrated is a light conducting rod 30 having a diffused stripe 31 on the bottom thereof such that radiation applied through the target 25 from the scanner 10 will be scattered and internally reflected in the rod 30 and applied to the face of the photomultiplier tube 32. Another type of receiver which may be employed is shown and described in U.S. Pat. No. 3,900,265 which is assigned to the assignee of the present invention.

As in typical light inspection systems, at any instant of time during the scan, the detector 32 provides an output signal which is proportional to the transmission of the spot on the material 25 on which the laser beam 14 is impinging. Flaws occurring in the material 25 being examined change the output of the detector 32 due to the transmissive or scattering properties of the material being examined providing a means for indicating flaws in the material. As is previously pointed out, in a reflective system the receiver 30 would be positioned above the material 25 to receive reflected radiation scattered or specularly reflected from the surface of the moving web 25.

Figure 2:
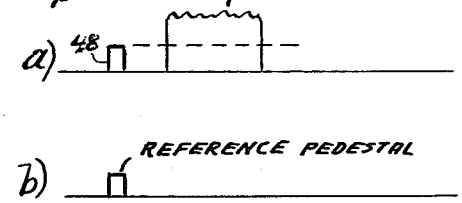
FIGS. 2a and 2b illustrates waveforms which are generated by and useful in the explanation of the operation of FIG. 1.

As a result of the scanned beam 14 passing across the product 25, the light energy collected by the receiver 30 will go from zero when off the product 25 to a finite amount when on the product by reason of the scattering or transmissive properties of the web and to zero again when off the product at the trailing edge which pedestal signal is shown in FIG. 2a. The electrical signal developed by the detector 32 is a classical rectangular function commonly referred to as a product pedestal signal. As long as the beam power, product equivalent optical density and receiver sensitivity remain fixed, the height of the product pedestal signal will remain fixed. If however, the beam power or the receiver sensitivity changes, the height of the pedestal will change, and it will not be known if the cause of the change is due to the product or is due to a power change or gain of the system.

In order to assure that the change in signal level of the detector is due solely to the product to thus produce an absolute dc system, the power gain of the system is stabilized by a control loop which includes the light source as well as the light collection system or receiver within the loop. Since the two systems parameters most subject to drift with time, temperature and other environmental properties are the laser beam power and the gain of the photomultiplier tube, a way for regulating the consequences of these changes is to couple a portion of the beam energy within the scanner directly to the face of the photomultiplier tube.

FIG. 1 illustrates one implementation of this in which a stabilized sensor 34, such as a solar cell or temperature compensated silicon detector, is positioned within or attached to the scanner 10 for converting the light signal in accordance with the intensity of the laser beam 14 into electrical form. The sensor output signal 34 is applied to an amplifier 36 whose amplitude is adjustable by a potentiometer 38 and the amplified output is applied to drive a light emitting diode 40 which is embedded within the receiver 30 in proximity to the face of the photomultiplier tube 32. Although it is preferable to embed the light emitting diode 40 close to the face of the PMT. FIG. 1 illustrates the positioning of the light emitting diode at different positions along the receiver 30, if it is desired to do so. The adjustment of the potentiometer 38 is equivalent to setting different reference levels, and thus controlling the sensitivity of the system which is desirable when examining different product types.

In order for the stabilized sensor 34 to function for its intended purpose, it is necessary to sample electronically the signal generated by the detector so that its level can be compared with an adjustable voltage reference. The difference signal thus formed is amplified and applied to an appropriate component within the system to provide a constant power gain. An appropriate element for this purpose is the high voltage power supply associated with the photomultiplier tube 32. The gain of the photomultiplier 32 is directly related to the high voltage applied to the tube. Accordingly, changes in laser beam power, photomultiplier tube sensitivity or other components within the loop are therefore corrected in the illustrated embodiment of FIG. 1 by a feedback system resulting in a fixed system sensitivity capable of measuring absolute changes in product characteristics.

The sensor output 34 is applied via PMT 32 to a sample and hold circuit 42. Once per facet timing pulses 44 (1/f) are applied from the rotary scanner 20 to an adjustable one shot multivibrator 46 which samples the output from the sensor 34 from the composite PMT output. This reference sample pedestal 48 is illustrated in FIG. 2b and is applied from the sample and hold circuit 42 to a differential amplifier 50 having a reference potential 52 applied to the other input thereof. Difference output representing changes in the level of the reference pedestal 48 is applied to the PMT high voltage power supply 54 whose output is coupled to the PMT 32. Accordingly, changes in laser beam power, PMT sensitivity and other components within the loop including the PMT high voltage power supply 54 are therefore compensated via the feedback system which stabilizes the gain of the system.

Placing the sensor 34 within the scanner 10 and coupling its output directly to the face of the photomultiplier tube 32 eliminates the need for excessive overscan of the scanner as well as removes the detector 34 and it associated output from influences of the external environment.

Figure 3:
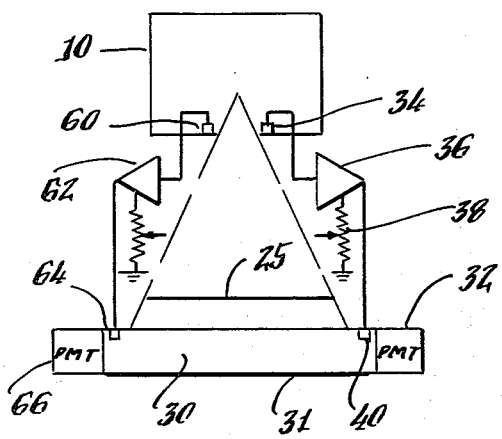
FIG. 3 is a diagrammatic illustration of the use of the present invention when two photomultiplier tubes are utilized in the receiver.

FIG. 3 illustrates a receiver 30 which employs two photomultiplier tubes thereby including a photomultiplier tube 66 in addition to the photomultiplier tube 32. In such an application, it is desirable although not absolutely necessary that a second stabilized sensor 60 be employed and be positioned on each side of the product corresponding to the leading and trailing edges of the moving web 25. As is illustrated in FIG. 3, the output of the sensor 60 is applied to an amplifier 62 and to a light emitting diode 64 positioned adjacent the face of the photomultiplier tube 66. In this embodiment two control systems of the type illustrated in FIG. 1, namely two closed loops, one for each photomultiplier tube would be required.

Figure 4:
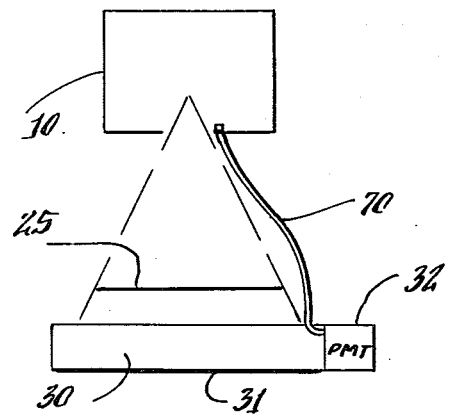
FIG. 4 is a diagrammatic illustration of the use of a light pipe for the derivation of a reference pedestal in accordance with the present invention.

Another embodiment of the present invention is illustrated in FIG. 4 which in effect is the simplest implementation of coupling a reference source of light directly from the laser beam to the photomultiplier tube in the form of an optical fiber or light pipe coupled from the edge limits of the scanned interval as illustrated by the light pipe 70 in FIG. 4. A light pipe would therefore be coupled to the PMT during an overscan and the resultant pedestal signal 48 as illustrated in FIG. 2b would be treated in the same manner by the control system as illustrated in FIG. 1. The amount of light coupled into the light pipe 70 can be controlled by a field stop thus providing a desired adjustment for referencing different product types and receiver configurations. It will be apparent of course that an additional light pipe can be utilized on the other side of the scanner for providing light pulses in both the leading and trailing edges of the target 25 which can be used with two PMT detectors in accordance with the embodiment of FIG. 3 or may be used with one as desired.

Figure 5:
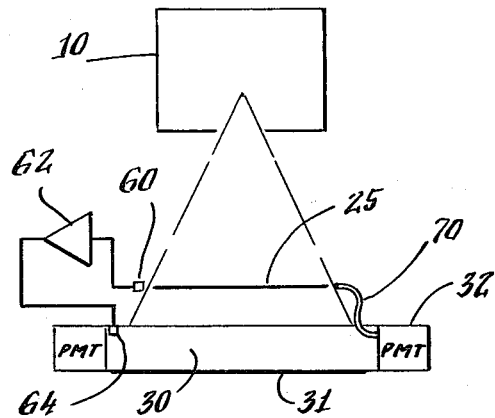
FIG. 5 is a diagrammatic illustration of alternative embodiments of the present invention in which the light pipe or photodetector are positioned adjacent the leading and trailing edges of the scanned target area.

FIG. 5 illustrates the positioning of the sensor 60 or the light pipe 70 along the leading and trailing edges of the target 25 which are hit by the overscan of the target. Again the sensitivity of the system is controlled by the closed loop arrangement shown in FIG. 1. The purpose of this illustration is merely to show that the sensors or the light pipes which ever are used may be positioned adjacent the target as distinguished from their positioning in the scanner as illustrated in the previous embodiments. Of course, the benefit of removing the generated reference pedestal from the external environment is somewhat diminished in this embodiment.

Since other changes and modifications varied to fit particular operating requirements and environments will be apparent to those skilled in the art, the invention is not considered limited to the examples chosen for purposes of illustration, and covers all changes and modifications which do not constitute a departure from the true spirit and scope of this invention.

What is claimed is:

1. A stabilized absolute direct current system for controlling the sensitivity of a light inspection system having a laser generating a laser beam and a scanner for scanning said laser beam over a surface of a moving material being inspected thereby to detect flaws in said material comprising:

a receiver for collecting laser beam radiation emanating from said material, said receiver having a photomultiplier tube for detecting and generating signals in accordance with the intensity of radiation applied thereto, means for applying a sample of radiation from said laser beam to said photomultiplier tube for generating a reference pedestal signal dependent on the intensity of said laser beam which is free of the influence of the characteristics of the material, comparator means having a reference potential and said reference pedestal signal applied thereto for deriving a control signal, a power supply for said photomultiplier tube, a closed loop feedback circuit for coupling said control signal to said power supply and coupling said power supply to said photomultiplier tube for automatically regulating the power gain to said photomultiplier tube to a constant value thereby providing a stabilized dc system.

2. The stabilized absolute direct current light inspection system set forth in claim 1 wherein said means for applying a sample of radiation from said laser beam to said photomultiplier tube comprises a light pipe.

3. The stabilized absolute direct current light inspection system set forth in claim 2 in which said light pipe is positioned at one end thereof in said scanner and on the other end thereof in said receiver for coupling radiation on the overscan of said scanner directly to said receiver.

4. The stabilized absolute direct current light inspection system set forth in claim 2 in which said light pipe is positioned on one end thereof adjacent an edge of said moving web and on the other end thereof in said receiver for coupling radiation on the overscan of said scanner directly to said receiver.

5. The stabilizer absolute direct current light inspection system set forth in claim 1 wherein said means for applying a sample of radiation from said laser beam to said photomultiplier tube comprises a sensor for detecting light from said laser beam, an amplifier coupled to said sensor for amplifying the signal generated by said sensor and a light emitting diode positioned in said receiver and coupled to the output of said amplifier.

6. The stabilized absolute direct current light inspection system set forth in claim 5 in which said sensor is positioned in said scanner.

7. The stabilized absolute direct current light inspection system set forth in claim 6 in which said sensor is positioned adjacent an edge of said moving material.

\* \* \* \* \*